United States Patent [19]
Yoon

[11] Patent Number: 5,607,439
[45] Date of Patent: *Mar. 4, 1997

[54] SAFETY PENETRATING INSTRUMENT WITH PENETRATING MEMBER MOVING DURING PENETRATION AND TRIGGERED SAFETY MEMBER PROTRUSION

[76] Inventor: InBae Yoon, 2101 Highland Ridge Dr., Phoenix, Md. 21131

[ * ] Notice: The term of this patent shall not extend beyond the expiration date of Pat. No. 5,431,635.

[21] Appl. No.: 315,506

[22] Filed: Sep. 30, 1994

Related U.S. Application Data

[63] Continuation-in-part of Ser. No. 83,220, Jun. 24, 1993, Pat. No. 5,431,635, Ser. No. 83,728, Jun. 29, 1993, Pat. No. 5,466,224, and Ser. No. 115,152, Sep. 2, 1993.

[51] Int. Cl.$^6$ ..................... A61M 5/00
[52] U.S. Cl. ............. 606/185; 604/165; 604/170
[58] Field of Search ............... 128/751, 752, 128/753, 754; 604/95, 158, 162, 163, 164, 165, 170, 272, 274, 280, 169; 606/167, 171, 185

[56] References Cited

U.S. PATENT DOCUMENTS

| | | |
|---|---|---|
| 1,087,865 | 2/1914 | Stevens . |
| 1,213,001 | 1/1917 | Philips . |
| 1,248,492 | 12/1917 | Hill . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,828,547 | 5/1989 | Sahl et al. . |
| 4,869,717 | 9/1989 | Adair . |
| 4,902,280 | 2/1990 | Lander . |
| 4,931,042 | 6/1990 | Holmes et al. . |
| 4,943,280 | 7/1990 | Lander . |
| 5,030,206 | 7/1991 | Lander . |

(List continued on next page.)

FOREIGN PATENT DOCUMENTS

| | | |
|---|---|---|
| 2544262 | 4/1977 | Germany . |
| 878265 | 11/1981 | U.S.S.R. . |
| 897224 | 1/1982 | U.S.S.R. . |
| 1435246 | 11/1988 | U.S.S.R. . |
| 904635 | 8/1962 | United Kingdom . |
| 9304632 | 3/1993 | WIPO . |
| 9304715 | 3/1993 | WIPO . |
| 9304716 | 3/1993 | WIPO . |
| 9317626 | 9/1993 | WIPO . |

*Primary Examiner*—Guy V. Tucker

[57] ABSTRACT

A safety penetrating instrument for penetrating an anatomical cavity wall to gain access to an anatomical cavity includes a cannula, a penetrating member having a distal end for penetrating an anatomical cavity wall to gain access to an anatomical cavity, and a safety member in the form of a safety shield or probe. The penetrating member is mounted on a bias member for biasing the penetrating member distally toward a rest position while allowing proximal movement of the penetrating member away from the rest position. Both the safety member and the cannula have distal ends movable between respective extended positions disposed distally of the penetrating member distal end to protect the penetrating member distal end and respective retracted positions disposed proximally of the penetrating member distal end to expose the penetrating member distal end. Extending mechanisms move the safety member and cannula distally to their respective extended positions and permit the safety member and cannula to move proximally to their respective retracted positions. The safety member and cannula are locked in the retracted positions to prevent movement to the extended positions during penetration of the anatomical cavity wall and are released responsive to movement of the penetrating member distally toward the rest position upon penetration into the anatomical cavity.

10 Claims, 4 Drawing Sheets

U.S. PATENT DOCUMENTS

| | | |
|---|---|---|
| 5,053,016 | 10/1991 | Lander . |
| 5,066,288 | 11/1991 | Deniega et al. . |
| 5,073,169 | 12/1991 | Raiken . |
| 5,104,382 | 4/1992 | Brinkerhoff et al. . |
| 5,104,383 | 4/1992 | Stichman . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,152,754 | 10/1992 | Plyey et al. . |
| 5,158,552 | 10/1992 | Borgia et al. . |
| 5,207,647 | 5/1993 | Phelps . |
| 5,215,526 | 6/1993 | Deniega et al. . |
| 5,224,951 | 7/1993 | Freitas . |
| 5,224,952 | 7/1993 | Deniega et al. . |
| 5,226,426 | 7/1993 | Yoon . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 11/1993 | Deniega . |
| 5,275,583 | 1/1994 | Crainich . |
| 5,290,243 | 3/1994 | Chodorow et al. . |
| 5,290,304 | 3/1994 | Storace . |
| 5,295,993 | 3/1994 | Green . |
| 5,312,354 | 3/1994 | Allen et al. . |
| 5,318,580 | 6/1994 | Gresl . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,346,459 | 9/1994 | Allen et al. . |
| 5,350,393 | 9/1994 | Yoon . |
| 5,360,405 | 11/1994 | Yoon . |
| 5,364,372 | 11/1994 | Danks et al. . |
| 5,366,445 | 11/1994 | Haber et al. . |
| 5,368,607 | 11/1994 | Freitas . |
| 5,372,588 | 12/1994 | Farley et al. . |
| 5,374,252 | 12/1994 | Banks et al. . |
| 5,376,082 | 12/1994 | Phelps . |
| 5,380,288 | 1/1995 | Hart et al. . |
| 5,383,859 | 1/1995 | Sewell, Jr. et al. . |
| 5,431,635 | 7/1995 | Yoon ........................................ 604/165 |

SAFETY PENETRATING INSTRUMENT WITH PENETRATING MEMBER MOVING DURING PENETRATION AND TRIGGERED SAFETY MEMBER PROTRUSION

CROSS-REFERENCE TO RELATED APPLICATIONS

This application is a continuation-in-part of prior applications Ser. No. 08/083,220, filed Jun. 24, 1993, now U.S. Pat. No. 5,431,635, Ser. No. 08/083,728, filed Jun. 29, 1993, now U.S. Pat. No. 5,466,224, and Ser. No. 08/115,152, filed Sep. 2, 1993, still pending, the disclosures of which are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While protruding safety penetrating instruments have been well received, there is room for improvement in reducing the force required to penetrate the cavity wall which necessarily includes the force required to overcome the spring bias on the safety member as well as the resistance of the cavity wall and insuring that the safety member protrudes which normally requires increasing the spring bias on the safety member and, thus, the force to penetrate. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

SUMMARY OF THE INVENTION

Accordingly, it is a primary object of the present invention to improve safety penetrating instruments of the type having a penetrating member and a safety member biased distally to protrude beyond the distal end of the penetrating member by easing penetration and assuring protrusion of the safety member.

Another object of the present invention is to reduce the force-to-penetrate required to penetrate an anatomical cavity wall with a safety penetrating instrument of the type having a distally biased safety member with a distal end for protruding beyond a distal end of a penetrating member once penetration into the cavity has been achieved.

A further object of the present invention is to increase the force biasing a safety member distally in a safety penetrating instrument to assure protrusion of the safety member after penetration into an anatomical cavity without increasing the force-to-penetrate required for penetration.

The present invention has an additional object to use both a cannula and a safety shield or probe as safety members in a safety penetrating instrument and to trigger movement of the safety members from retracted positions exposing the distal end of a penetrating member to extended positions protruding beyond the distal end of the penetrating member in response to distally-biased movement of the penetrating member upon penetrating into an anatomical cavity.

Some of the advantages of the safety penetrating instrument of the present invention are that the distal bias force on respective safety members can be designed to assure protrusion of the safety members upon penetration regardless of the anatomical cavity being penetrated, that the force-to-penetrate of the safety penetrating instrument can be minimized to permit use in delicate tissue, that release of the safety members for movement to the extended protruding position can be triggered by slight distal movement of the penetrating member in response to penetration through the tissue, and that the safety penetrating instrument can be inexpensively manufactured with minimum components to reduce cost, facilitate sterilization for re-use and allow economical single-patient use.

The present invention is generally characterized in a safety penetrating instrument including a cannula, a penetrating member having a distal end for penetrating an anatomical cavity wall to gain access to an anatomical cavity, and a safety member in the form of a safety shield or probe. The penetrating member is mounted on a bias member for biasing the penetrating member distally toward a rest position while allowing proximal movement of the penetrating member away from the rest position. Both the safety member and the cannula have distal ends movable between respective extended positions disposed distally of the penetrating member distal end to protect the penetrating member distal end and respective retracted positions disposed proximally of the penetrating member distal end to expose the penetrating member distal end. Extending means are provided for moving the safety member and cannula distally to their respective extended positions and for permitting the safety member and cannula to move proximally to their respective retracted positions. Means are also provided for manually moving the safety member and cannula proximally from their respective extended positions to their respective retracted positions and for locking the safety member and cannula in the retracted positions to prevent movement of the safety member and cannula to the extended positions during penetration of the anatomical cavity wall. Releasing means responsive to movement of the penetrating member distally toward the rest position upon penetration into the anatomical cavity triggers release of the locking means to permit the extending means to move the safety member and cannula to their respective extended positions.

Other objects and advantages of the present invention will become apparent from the following description of the preferred embodiments taken in conjunction with the accompanying drawings wherein, unless specified otherwise, like parts or parts that perform like functions are identified in each of the several figures by the same reference character or by reference characters sharing the same last two digits.

DESCRIPTION OF THE PREFERRED EMBODIMENTS

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

Figure 1:
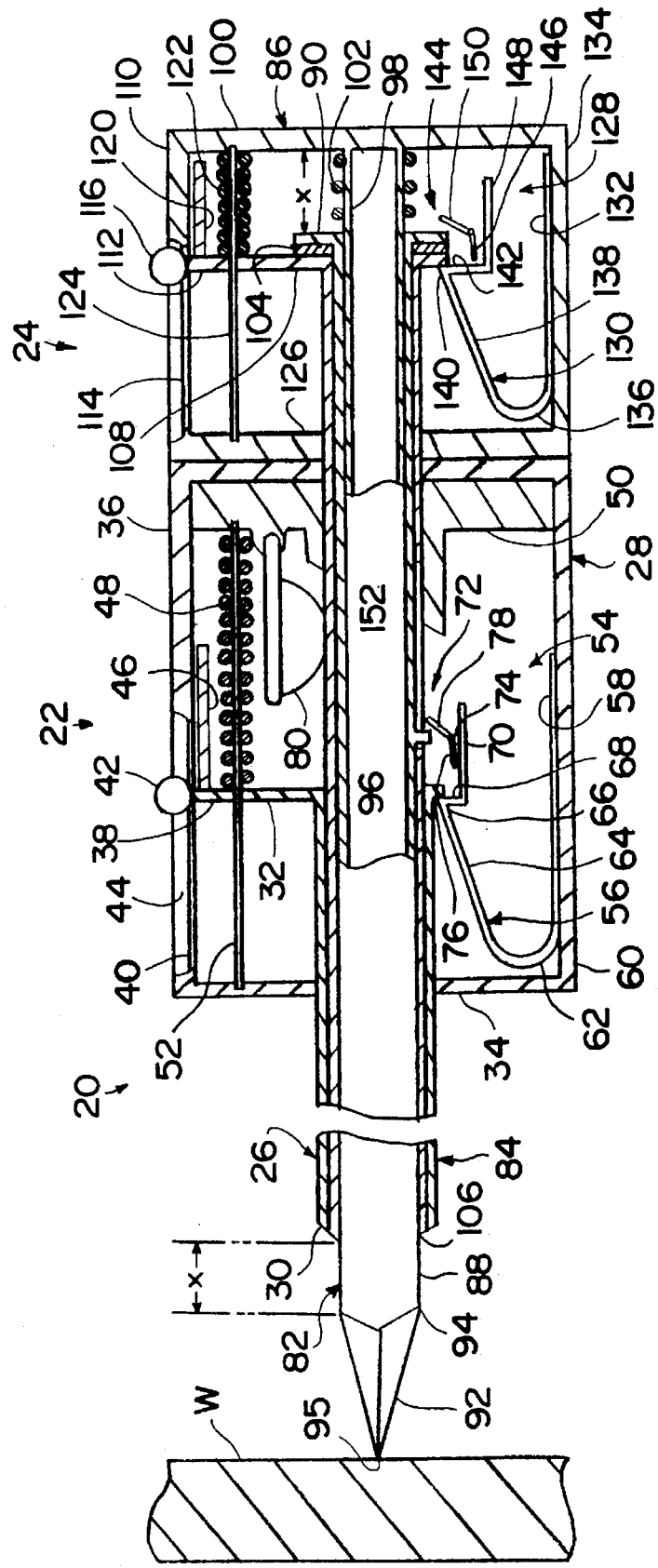
FIG. 1 is a broken side view, partly in section, of a safety penetrating instrument according to the present invention.

A safety penetrating instrument 20 according to the present invention, as shown in FIG. 1, is formed of a portal unit 22 and a penetrating unit 24. The portal unit 22 can be made of any desirable, medical grade materials depending on procedural use and desirability of being for single patient use or re-usable and includes an elongate portal sleeve, cannula or catheter 26 and a housing 28 mounting a proximal end of portal sleeve 26. Portal sleeve 26 terminates distally at a distal end 30 and proximally at a transverse flange 32 disposed in housing 28 with the portal sleeve passing through an opening in a front wall 34 of the housing. Portal sleeve 26 can have any desirable cross-sectional configuration, including cylindrical or tubular configurations, in accordance with the procedure to be performed and the anatomical cavity to be penetrated. Preferably, portal sleeve 26 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving a penetrating member of penetrating unit 24.

Flange 32 extends toward an upper wall 36 of housing 28, and a pin 38 extends from flange 32 through a slot 40 in the housing upper wall 36 to terminate at a handle or knob 42 positioned in an elongate, trough-like recess 44 in the housing upper wall. Slot 40 and recess 44 extend longitudinally in parallel with the longitudinal axis of the safety penetrating instrument 20, and an indicator strip 46 extends proximally, perpendicularly from flange 32 to be visible through and along the length of slot 40 when the portal sleeve is in an extended protruding position as will be described further below. The indicator strip 46 can be colored and/or can be provided with any desirable indicia, and the slot 40 or the recess 44 can be provided with a transparent window or cover for viewing of the indicator strip therethrough.

An extending member 48 is mounted between portal sleeve flange 32 and a rear wall 50 of housing 28 to bias the portal sleeve 26 in a distal direction to an extended protruding position where distal end 30 of the portal sleeve is disposed beyond a penetrating distal end of the penetrating member as will be explained further below. The extending member can include a helical coil spring 48 mounted in compression between portal sleeve flange 32 and the housing rear wall 50 as shown, or the extending member can include any other type of spring or other bias device. If desired, a guide rod 52 can be connected between the front wall 34 and the rear wall 50 of housing 28 with the extending spring 48 disposed around the guide rod.

A locking and releasing mechanism 54 for locking the portal sleeve in a retracted position, shown in FIG. 1, exposing the distal end of the penetrating member, and for releasing the portal sleeve to allow the portal sleeve to move to the extended protruding position, includes a latch or locking spring 56, made of a strip of resilient material, formed to have a substantially flat base 58 secured to a bottom wall 60 of housing 28 and a bend 62 joining the base 58 with an upwardly angled arm 64 spaced from the base. Arm 64 carries or forms a latch 66 having a distal angled latching surface joining a proximal latching surface 68 disposed substantially transverse to the longitudinal axis of the safety penetrating instrument and substantially parallel to the portal sleeve flange 32. Arm 64 has an extension 70 positioned proximally of latch 66, and a releasing member or trigger 72 is juxtaposed with extension 70. The trigger 72 is pivotally mounted in the housing on a pin 74 secured to a wall or walls of the housing or structure supported in the housing, and the trigger is generally L-shaped with a leg 76 overlying extension 70 and a leg 78 extending transversely from leg 76 but at a slight angle toward the proximal end of the safety penetrating instrument. A torsion spring (not shown) is coiled around pin 74 and fixed to trigger 72 to bias the trigger counterclockwise, looking at FIG. 1, such that leg 76 is biased toward extension 70.

The portal sleeve distal end 30 can have various configurations to protect tissue within an anatomical cavity by covering or surrounding the distal end of the penetrating member in the extended protruding position; and, as shown, the portal sleeve distal end defines an annular or peripheral edge having a relatively blunt chamfered configuration to protect tissue within the anatomical cavity.

The housing 28 can be made of any desirable material and can have any desirable configuration to facilitate grasping by a user and includes a rear wall having an opening therein aligned with the opening in the housing front wall to allow passage therethrough by the penetrating member. The housing 28 is preferably constructed to sealingly engage instruments passing therethrough and to include a valve biased to a closed state when no instrument passes through the portal sleeve. A flapper valve 80 is shown; however, any suitable valve construction can be utilized, for example, trumpet or nipple valves.

The penetrating unit 24 includes a penetrating member 82, a safety shield 84 and a hub 86 mounting proximal ends of the penetrating member and safety shield. Penetrating member 82 includes an elongate shaft or body 88 having a proximal flange 90 mounted by the hub 86, a distal end 92 extending from a transverse dimensional transition 94 in the penetrating member body to a tissue penetrating tip 95, and a transverse protrusion 96 disposed intermediate the proximal and distal penetrating member ends. The penetrating member body is at least partially hollow and is telescopically fitted over a guide tube 98 secured to a rear wall 100 of the hub 86. A bias member 102 is connected between penetrating member flange 90 and the hub rear wall 100 to bias the penetrating member distally toward a rest position where flange 90 abuts a transverse wall 104 secured to one or more walls of the hub 86 and having an opening for passage of the penetrating member body 88 therethrough. Bias member 102 is shown as a helical coil spring disposed around the guide tube 98 and held in compression between the penetrating member flange 90 and the rear wall 100 of the hub, but can include various other types of springs as well as other types of bias devices including compression springs, tension springs, torsion springs, pan springs, leaf springs, rubber, plastic or magnets, for example.

The penetrating member distal end 92 can have any configuration desired by a user for a particular procedure, for example, the pyramidal trocar configuration shown or conical, threaded, multi-faceted or open, slanted or needle configurations. The penetrating member 82 can be made of any suitable, medical grade materials and can be made of multiple components such that, for example, the distal end 92 is made of stainless steel and secured in any conventional manner, such as by threaded engagement, to the distal end of the body or shaft, which can be tubular and made of a less expensive material, such as plastic or metal. Hub 86 can be made of any desirable medical grade material and can have any desired configuration in cross-section to facilitate grasping of the hub and the housing by a user with one hand.

Safety shield 84 is disposed between the penetrating member 82 and the portal sleeve 26 when hub 86 is mated with housing 28. The safety shield 84 terminates distally at a distal end 106 and proximally at a transverse flange or plate 108 disposed in hub 86. A tubular safety shield is shown; however, safety shield 84 can have any desirable configuration in cross-section to couple safety shield distal end 106 with flange 108. Flange 108 extends toward an upper wall 110 of hub 86, and a pin 112 extends from flange 108 through a slot 114 in the hub upper wall 110 to terminate at a handle or knob 116 positioned in an elongate, trough-like recess in the hub upper wall. Slot 114 extends longitudinally in parallel with the longitudinal axis of the safety penetrating instrument 20, and an indicator strip 120 extends proximally, perpendicularly from flange 108 to be visible through and along the length of slot 114 when the safety shield is in the extended protruding position. An extending member 122 including a helical coil spring is connected between flange 108 and the rear wall 100 of hub 86 to bias the safety shield to an extended protruding position where the distal end 106 of the safety shield is disposed beyond the distal end 92 of the penetrating member; and, if desired, the spring can be disposed around a guide rod 124 connected between forward and rearward walls 126 and 100 of the hub.

Penetrating unit 24 also includes a locking and releasing mechanism 128 for locking the safety shield 84 in a retracted position exposing the distal end 92 of the penetrating member 82 and releasing the safety shield to allow the safety shield to move to the extended protruding position. Locking and releasing mechanism 128 is similar to locking and releasing mechanism 54 except that the trigger for locking and releasing mechanism 128 is disposed proximally of the penetrating member flange 90 when the penetrating member flange abuts transverse wall 104.

The latch or locking spring 130 for locking and releasing mechanism 128 is made of a strip of resilient material formed to have a substantially flat base 132 secured to a bottom wall 134 of hub 86 and a bend 136 joining the base 132 with an angled arm 138. Arm 138 carries latch 140 which has a distal angled latching surface joining a proximal latching surface 142 disposed substantially transverse to the longitudinal axis of the safety penetrating instrument and substantially parallel to the safety shield flange 108. Trigger 144 is juxtaposed with arm extension 148 to be disposed proximally of latch 140 and is similar to trigger 72 with a leg 146 overlying extension 148 and a leg 150 extending substantially transversely from leg 146 but at a slight angle toward the proximal end of the safety penetrating instrument. Trigger 144 is biased counterclockwise, looking at FIG. 1, such that leg 146 is biased toward extension 148.

A longitudinal slot 152 is formed intermediate the proximal and distal safety shield ends for passage of the penetrating member protrusion 96. When penetrating member 82 is in the rest position and flange 90 abuts transverse wall 104, protrusion 96 extends through slot 152 in the safety shield to be disposed distally of leg 78 of trigger member 72 in housing 28. Slot 152 is of suitable length for safety shield 84 to be fully extended before protrusion 96 abuts the proximal end of the slot.

The portal unit 22 and the penetrating unit 24 can be provided to a user separately or assembled together as shown in FIG. 1, and either or both of the portal and penetrating units can be manufactured in a manner to be disposable for single patient use or to be sterilizable for re-use. The hub 86 can be coupled to the housing 28 by suitable detent or latch mechanisms if desired, and the penetrating unit can be withdrawn from the portal unit leaving the portal sleeve 26 in place within an anatomical cavity to serve as a portal for introducing medical instruments therethrough.

Figure 3:
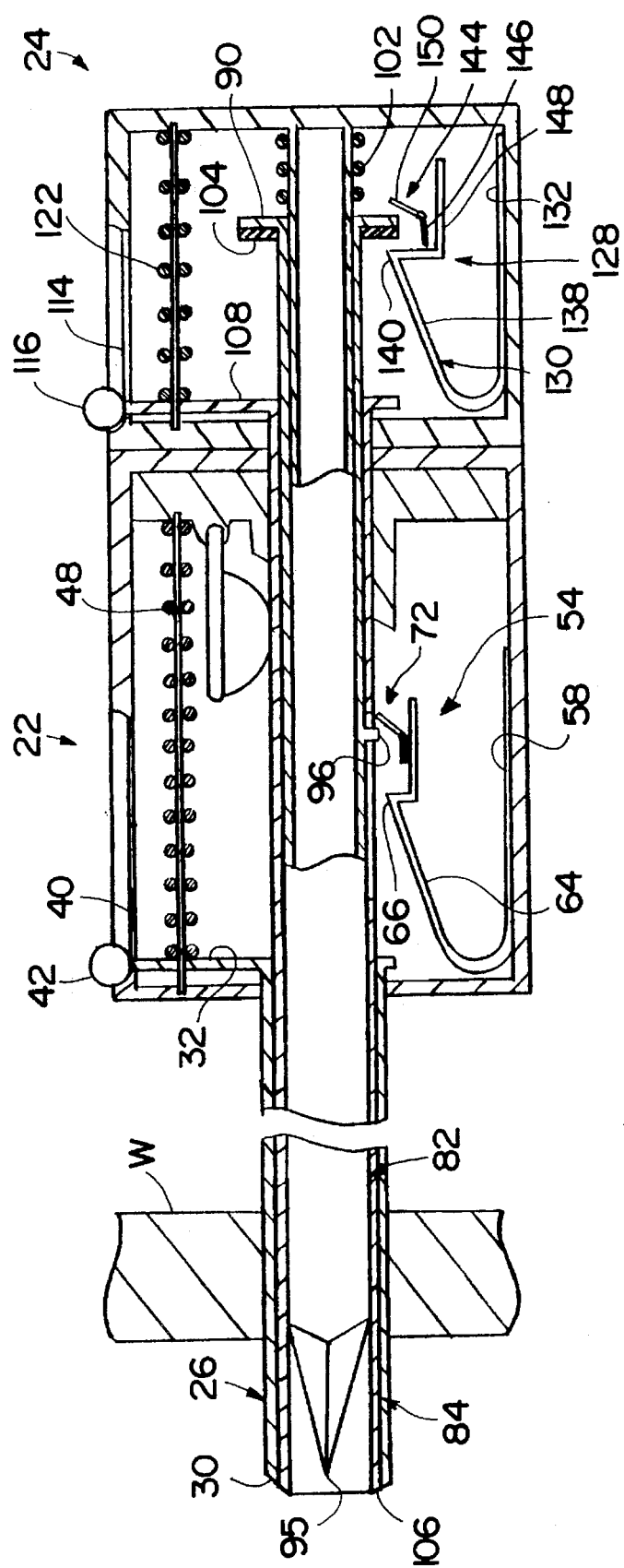
FIG. 3 is a broken side view, partly in section, of the safety penetrating instrument of FIG. 1 following penetration into the anatomical cavity.

Prior to use, the safety penetrating instrument 20 is in the condition shown in FIG. 3 with the portal sleeve 26 and the safety shield 84 in their extended protruding positions protecting the sharp distal tip 95 of the penetrating member 82. With the safety penetrating instrument 20 in the condition shown in FIG. 3, handle 42 will be disposed at a distal end of slot 40 due to the bias of portal sleeve extending member 48 with indicator strip 46 viewable along the length of the slot 40. Similarly, handle 116 will be disposed at a distal end of slot 114 in the hub due to the bias of safety shield extending member 122. Prior to commencing penetration of an anatomical wall W, handles 42 and 116 are grasped individually or together and manually moved proximally to move the portal sleeve 26 proximally against the bias of the extending member 48 until the portal sleeve flange 32 rides over latch 66 by engaging the distal latching surface to move arm 64 toward base 58 and to move the safety shield 84 proximally against the bias of extending member 122 until the safety shield flange 108 rides over latch 140 by engaging the distal latching surface to move arm 138 toward base 132. At this time, the user can feel the respective flanges locking into place in engagement with proximal latching surfaces as the spring arms spring back and can also visually determine that the portal sleeve and safety shield are locked in their respective retracted positions by noting the position of handles 42 and 116 at proximal ends of slots 40 and 114 at which time indicator strips will no longer be visible or will be only slightly visible through the slots.

The safety penetrating instrument 20 is now in the position illustrated in FIG. 1 with the portal sleeve 26 and safety shield 84 locked in retracted positions by locking and releasing mechanisms 54 and 128, respectively, and the penetrating member 82 extending beyond the distal ends of the portal sleeve and safety shield. With the portal sleeve 26 and safety shield 84 locked in their retracted positions, the portal sleeve and safety shield distal ends will be disposed proximally of the penetrating member transition 94 a distance X approximately equal to the spacing between transverse wall 104 and hub rear wall 100.

Figure 2:
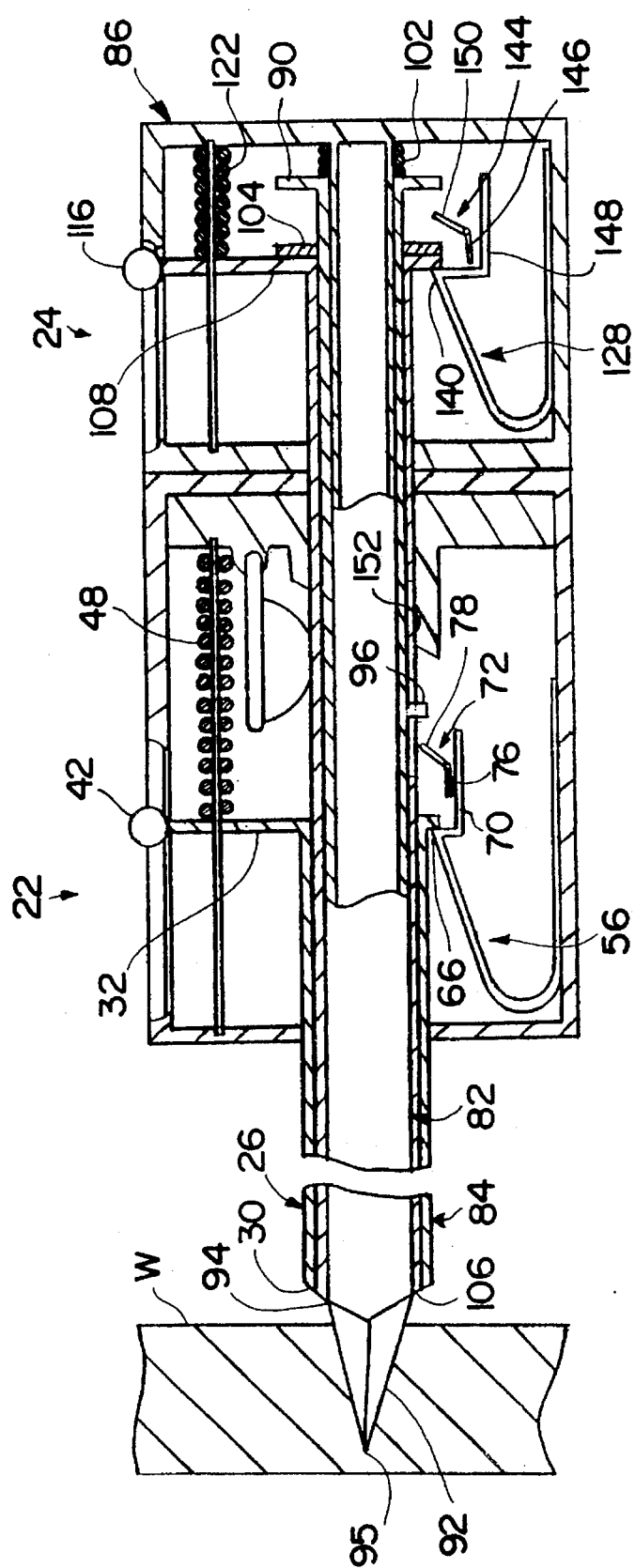
FIG. 2 is a broken side view, partly in section, of the safety penetrating instrument of FIG. 1 during penetration of a wall of an anatomical cavity.

As penetration of the anatomical cavity wall W is commenced, the force-to-penetrate is limited to the force required to cause penetrating member distal end 92 to pass through the cavity wall W. As penetration continues, the safety penetrating instrument will advance through the cavity wall W as shown in FIG. 2, and the force from tissue contact on the distal end of the penetrating member 82 will cause the penetrating member to move proximally causing the operating member formed by flange 90 to move proximally until flange 90 abuts the rear wall of hub 86 which serves as a stop or abutment limiting proximal movement of the penetrating member. As the flange 90 moves proximally, the operating member formed thereby engages leg 150 to pivot trigger 144 clockwise, looking at FIG. 2, allowing the operating member to pass thereby. The clockwise pivotal movement of trigger 144 does not cause movement of the latch 140 since there is no engagement by either leg 146 or 150 with arm extension 148. Once the operating member passes by leg 150, a torsion spring or the like returns trigger 144 to its normal position with leg 146 adjacent arm extension 148. Accordingly, during penetration of the anatomical cavity wall W, no force is required to overcome the bias of extending member 122.

Similarly, as the transverse penetrating member protrusion 96 moves proximally, the operating member formed thereby engages leg 78 of trigger 72 in housing 28 to pivot trigger 72 clockwise, looking at FIG. 2, to allow the protrusion to pass thereby. The clockwise pivotal movement of trigger 72 does not cause movement of the latch 66 since there is no engagement by either leg 76 or 78 with arm extension 70. Once the protrusion passes by leg 78, a torsion spring on the leg returns trigger 72 to its normal position with leg 76 adjacent arm extension 70.

Once the distal end 92 of the penetrating member 82 has passed through the cavity wall W, a reduction in the force from tissue contact on the distal end of the penetrating member will allow the penetrating member to move distally under the influence of bias member 102. As the penetrating member 82 moves distally, flange 90 engages leg 150 of trigger 144 causing the trigger to pivot counterclockwise looking at FIG. 3 and causing leg 146 to engage arm extension 148 moving arm 138 toward base 132 against the force of spring strip 130. The movement of arm 138 away from the longitudinal axis of the safety penetrating instrument causes latch 140 to move out of engagement with the safety shield flange 108 thereby allowing extending member 122 to move the safety shield distally to the extended protruding position where distal end 106 protrudes beyond the sharp distal tip 95 of the penetrating member as illustrated in FIG. 3 thereby protecting tissue within the anatomical cavity from inadvertent contact with the sharp distal tip 95. At the same time, distal movement of penetrating member 82 causes protrusion 96 to engage leg 78 of trigger 72 in housing 28 causing the trigger to pivot counterclockwise and causing leg 76 to engage arm extension 70 moving arm 64 toward base 58 against the force of spring strip 56. The movement of arm 64 away from the longitudinal axis of the safety penetrating instrument causes latch 66 to move out of engagement with the portal sleeve flange 32 thereby allowing extending member 48 to move the portal sleeve distally to the portal sleeve extended position where the distal end 30 of the portal sleeve protrudes beyond the sharp distal tip 95 of the penetrating member as illustrated in FIG. 3. With the distal end 30 of portal sleeve 26 in the anatomical cavity, the penetrating unit 24 including the penetrating member 82 and safety shield 84 can be withdrawn from the portal unit 22 leaving the portal sleeve in place such that instruments for performing endoscopic procedures can be introduced into the cavity via the portal formed by the portal unit 22.

Although the portal sleeve and safety shield are disclosed herein as being safety members, it will be appreciated that other members can be safety members, such as a safety probe disposed within the penetrating member to be movable through an aperture or opening in the penetrating member to protect the distal end thereof. By forming the portal sleeve and safety shield extending members to be relatively strong, protrusion of the safety members is assured even should one or both of the safety members engage tissue in the anatomical cavity wall or within the anatomical cavity or should any tissue be jammed between the safety member and the penetrating member and/or the portal sleeve. Additionally, the strong force of the extending springs provides the user with the psychological benefit of knowing that a safety member is protecting the penetrating member. Should tissue within the anatomical cavity be contacted by the distal end of one of the safety members, the safety member can bounce or give a little in the manner of a shock absorber to protect such contacted tissue. Movement of a safety member can be seen by the user by noticing movement of the handle toward a distal end of a slot and observation of an indicator strip if provided. The strong force of the extending springs also provides the user with an easily felt tactile signal that the safety member has moved to the extended position and that penetration into the cavity has occurred which also can be visually confirmed by the position of the handle and the indicator strip. The distal bias of spring 102 and/or the resistance of the anatomical tissue to penetration of the penetrating member need only be great enough to produce slight longitudinal movement of operating flange 90 and protrusion 96 past the triggers such that the force-to-penetrate is minimized.

From the above, it will be appreciated that the penetrating member of the safety penetrating instrument of the present invention is movable proximally against a distal bias during penetration of an anatomical cavity wall and that distally-biased movement of the penetrating member upon entering the anatomical cavity will trigger distal movement or protrusion of the cannula, a safety shield or probe, or both a cannula and a safety shield or probe to function as safety members protecting the distal end of the penetrating member. By "safety member" is meant any structure movable distally in relation to the penetrating member to protect the tip of the penetrating member within an anatomical cavity. Since in the safety penetrating instrument of the present invention both the cannula and a safety shield or probe can be extended to protect the penetrating member tip, each can function as a safety member upon penetration of the safety penetrating instrument into an anatomical cavity. The cannula can be a portal sleeve, a needle open at both ends with fluid flow therethrough, a catheter or any other tubular component of a medical instrument. The cannula is coupled with a safety member such as a tubular safety shield disposed between the cannula and the penetrating member, a safety probe fitted within a hollow penetrating member, or a component partly within and around the penetrating member and movable distally to protrude relative to the penetrating member to protect the distal end thereof when triggered. The cannula could also be coupled with a protective sheath or probe that is not triggered to protrude but which protects the distal end of the penetrating member after it is removed from the portal sleeve. Redundant safety can also be achieved by biasing the safety shield and/or cannula distally while allowing one or both to move proximally during penetration and triggering release of respective safety members in response to distal movement of one or more of the cannula, the safety shield and the penetrating member upon entry into the anatomical cavity. Additionally, the triggered safety member protrusion can be combined with penetrating member retraction to provide separate modes of safety.

In the embodiments shown, the distal end of the cannula and the distal end of the safety shield (or probe, if provided) are spaced proximally of a transverse dimensional transition in an outer surface of the penetrating member at the penetrating member distal end immediately prior to use in penetrating the anatomical cavity wall; and since the penetrating member is movable during penetration, the distal end of the penetrating member becomes displaced proximally during penetration and triggers safety member protrusion when returning distally toward the rest position upon entering the anatomical cavity. It will be appreciated, however, that the portal sleeve and safety shield distal ends can be aligned as shown or staggered when the portal sleeve and safety shield are in their retracted positions.

The components of the safety penetrating instrument of the present invention can be made of any suitable, medical grade materials to permit sterilization for re-use or for single patient use. The components can be made of multiple parts of various configurations and materials to reduce cost. The portal unit can have various valves, stop cocks and seals in the housing to control fluid flow therethrough, and conventional detent mechanisms can be used to connect or latch the hub with the housing when the portal unit and the penetrating unit are assembled. The distal ends of the cannula and the safety shield or probe can be chamfered or blunt, smooth or roughened, or have any other configuration depending on the need for ease of penetration or increased resistance; and when a safety shield or probe is provided it can be mounted either by the portal unit or the penetrating unit depending on the desirability of being left in place with the cannula or being withdrawn with the penetrating member.

Figure 4:
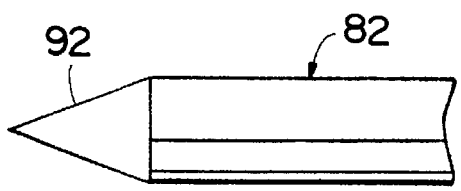
FIGS. 4–9 are side views of alternative distal configurations for the penetrating member of the safety penetrating instrument of the present invention.
Figure 5:
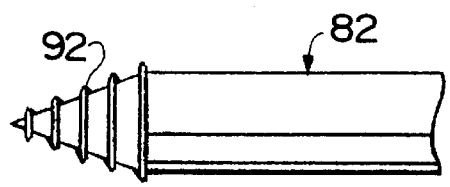
Figure 6:
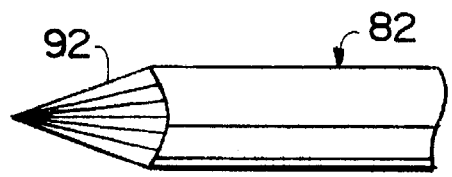
Figure 7:
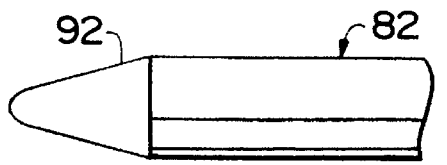
Figure 8:
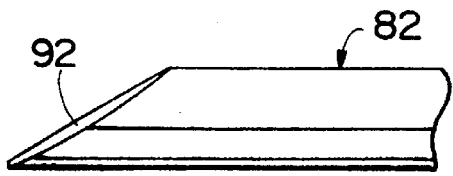
Figure 9:
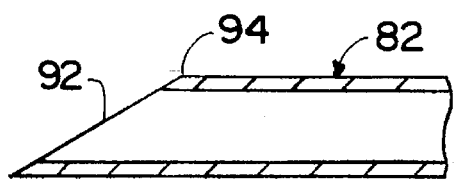

The penetrating member can be solid, hollow or partially solid and hollow, formed as single or multiple pieces, and movable telescopically over a guide tube as shown or being fixed at a proximal end with a movable distal end being biased. The distal end 92 of the penetrating member 82 can have any configuration desired for a particular procedure, for example, the pyramidal trocar configuration shown or a conical distal end (FIG. 4), a threaded distal end (FIG. 5), a multifaceted distal end (i.e., having two or more facets as shown in FIG. 6), a blunt distal end (FIG. 7), a slanted distal end (FIG. 8) or a hollow needle configuration with fluid flow therethrough (FIG. 9). Additionally, the surface defining the distal end of the penetrating member can be irregular or smooth, continuous or perforated, provided with cutting features or having any combination of the above features. If the penetrating member 82 is a hollow needle having a beveled end as shown in FIG. 9 or a curved Tuohey-type distal configuration, the proximal edge of the opening at the distal end 92 of the needle is considered the transverse dimensional transition 94 and thus the cannula and/or safety shield distal end is aligned with the distal end of the needle when located adjacent the proximal edge.

Figure 10:
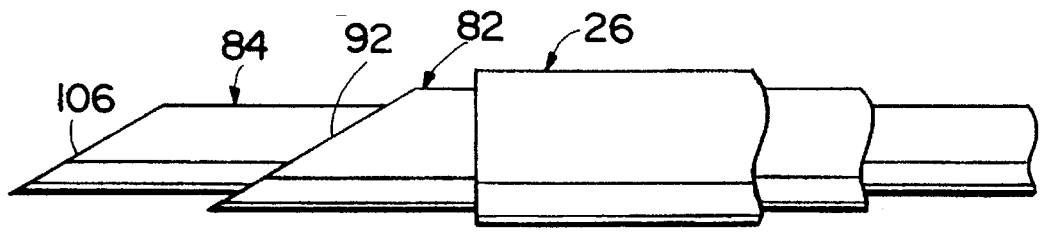
FIG. 10 is a side view of the distal end of a penetrating member configured to accommodate a safety probe.

As mentioned previously, the safety member of the present invention can be a tubular member such as the cannula or a safety shield disposed between the cannula and penetrating member, or in the case of a hollow penetrating member, the safety member can be a probe disposed at least partially within the penetrating member and movable through one or more apertures formed at or near the distal end of the penetrating member. FIG. 10 shows a cannula 26 surrounding a hollow penetrating member 82 with a beveled distal end 92 and a cylindrical safety probe 84 in an extended protruding position to protect the distal end of the penetrating member. The safety probe 84 has a beveled distal end 106 and is preferably movable from the extended position shown to a retracted position where the beveled distal end 106 of the safety probe 84 is flush with the distal end 92 of the penetrating member 82. It will be appreciated that a coaxial extending mechanism can be fitted within the penetrating member to bias the safety probe to the extended position or a flange carried at the safety probe proximal end and passed through a slot or opening in the penetrating member to be acted on by any of the extending mechanisms previously described. The safety probe distal end can have any configuration to protrude through single or multiple openings formed in the penetrating member distal end and can conform to the distal profile of the penetrating member or present a discontinuous surface.

The locking and releasing mechanisms require only a latch for locking the safety members in their retracted positions and a trigger for releasing the latch in response to distal movement of an operating member; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578, filed Apr. 15, 1992, Ser. No. 07/929,338, filed Aug. 14, 1992, Ser. No. 07/845,177, filed Sep. 15, 1992, Ser. No. 07,945, 177, filed Sep. 15, 1992, Ser. No. 08/079,586, filed Jun. 22, 1993, Ser. No. 08/195,512, filed Feb. 14, 1994, Ser. No. 08/196,029, filed Feb. 14, 1994, Ser. No. 08/196,027, filed Feb. 14, 1994, Ser. No. 08/195,178, filed Feb. 14, 1994, Ser. No. 08/237,734, filed May 4, 1994, Ser. No. 08/247,205, filed May 20, 1994, Ser. No. 08/254,007, filed Jun. 3, 1994 and Ser. No. 08/260,439, filed Jun. 15, 1994, the disclosures of which are incorporated herein by reference. The above applications disclose automatically retracting safety penetrating instruments such that modification of the locking and releasing mechanisms requires configuring the latches to lock a member in a retracted position rather than in an extended position. The above applications also disclose various bias arrangements useful with the safety penetrating instrument of the present invention. Other locking and releasing mechanisms that can be used in the safety penetrating instrument of the present invention are disclosed in applicant's related copending applications Ser. Nos. 08/279, 170 and 08/279,172, filed Jul. 22, 1994, the disclosures of which are incorporated herein by reference.

One or more control buttons, such as the control buttons described in applicant's copending patent application, Ser. No. 08/083,220, filed Jun. 24, 1993, can be mounted next to any latch for manually disengaging the latch to prevent locking of a corresponding safety member in the retracted position, thereby converting the safety penetrating instrument to a standard safety shielded penetrating instrument without triggered protrusion. In addition, any latch can carry a secondary pawl or protrusion at a distal end for locking a safety member in the extended position and can then be released through the use of a control button as described above.

The transverse protrusion 96 carried by the safety shield 84 can be integrally formed on an exterior surface of the safety shield as shown or can be mounted within the safety shield as part of a pivoted lever protruding through slots in the guide rod 98, penetrating member 82 and safety shield 84 to engage trigger 72 in housing 28. If part of a pivoted lever, the protrusion 96 can be made to withdraw into the safety shield 84 by rotating the lever, for example by use of a control button positioned adjacent the lever and operable to cam the lever in a manner to withdraw the protrusion.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in the wall of an anatomical cavity wall comprising a housing;

an elongate cannula mounted by said housing and having a distal end for positioning in the anatomical cavity and a proximal end for positioning externally of the anatomical cavity;

a penetrating member disposed in said cannula and having a distal end for penetrating the anatomical cavity wall;

cannula extending means for moving said cannula distally relative to said housing from a cannula retracted position where said cannula distal end is disposed proximally of said penetrating member distal end to a cannula extended position where said cannula distal end protrudes distally from said penetrating member distal end;

means for manually moving said cannula from said cannula extended position to said cannula retracted position;

cannula locking means for locking said cannula in said cannula retracted position to prevent distal movement of said cannula beyond said cannula retracted position;

bias means for biasing said penetrating member distally relative to said housing toward a rest position while permitting proximal movement of said penetrating member away from said rest position during penetration of the anatomical cavity wall;

a safety member disposed in said cannula and having a distal end, said safety member being movable relative to said housing between a safety member extended position wherein said safety member distal end protrudes distally from said penetrating member distal end and a safety member retracted position where said safety member distal end is disposed proximally of said penetrating member distal end to expose said penetrating member distal end;

safety member extending means for moving said safety member distally relative to said housing from said safety member retracted position to said safety member extended position;

means for manually moving said safety member proximally relative to said housing from said safety member extended position to said safety member retracted position;

safety member locking means for locking said safety member in said safety member retracted position during penetration of the anatomical cavity wall; and releasing means responsive to distally-biased movement of said penetrating member upon entering the anatomical cavity for triggering release of said cannula and safety member locking means to permit said cannula and safety member extending means to move said cannula and safety member distally relative to said housing from their respective retracted positions to their respective extended positions.

2. A safety penetrating instrument as recited in claim 1 wherein said safety member includes a safety shield disposed between said cannula and said penetrating member.

3. A safety penetrating instrument as recited in claim 1 wherein said safety member includes a safety probe disposed within said penetrating member.

4. A safety penetrating instrument as recited in claim 1 wherein said penetrating member extends distally from a proximal end, said safety member extends distally from a proximal end and further including a hub mounting said penetrating member proximal end and said safety member proximal end whereby said penetrating member and said safety member can be withdrawn from said cannula together by grasping said hub.

5. A safety penetrating instrument as recited in claim 1 wherein said penetrating member distal end extends distally from a transverse dimensional transition in said penetrating member and said safety member distal end is proximally spaced from said transition when said safety member is in said retracted position and said penetrating member is in said rest position.

6. A safety penetrating instrument as recited in claim 5 wherein said penetrating member distal end is movable proximally from said rest position to place said transverse dimensional transition into alignment with said safety member distal end when said safety member is in said retracted position.

7. A safety penetrating instrument as recited in claim 1 wherein said penetrating member distal end extends distally from a transverse dimensional transition in said penetrating member and said cannula distal end is located proximally of said transition when said cannula is in said retracted position and said penetrating member is in said rest position.

8. A safety penetrating instrument as recited in claim 7 wherein said penetrating member distal end is movable proximally from said rest position to place said transverse dimensional transition into alignment with said cannula distal end when said cannula is in said retracted position.

9. A safety penetrating instrument as recited in claim 1 wherein said cannula distal end and safety member distal end are spaced proximally of said penetrating member transition when said safety member and cannula are in said respective retracted positions and said penetrating member is in said rest position.

10. A safety penetrating instrument as recited in claim 9 wherein said penetrating member is movable proximally from said rest position to place said transverse dimensional transition into alignment with said retracted safety member and cannula distal ends.

* * * * *